United States Patent [19]

Krauter

[11] Patent Number: 5,047,848
[45] Date of Patent: Sep. 10, 1991

[54] ELASTOMERIC GAGE FOR BORESCOPE

[75] Inventor: Allan I. Krauter, Syracuse, N.Y.

[73] Assignee: Welch Allyn, Inc., Skaneateles Falls, N.Y.

[21] Appl. No.: 552,574

[22] Filed: Jul. 16, 1990

[51] Int. Cl.⁵ .............................................. H04N 7/18
[52] U.S. Cl. .................................... 358/100; 358/107; 33/501
[58] Field of Search ................ 358/100, 107, 98, 93, 358/139; 33/501

[56] References Cited

U.S. PATENT DOCUMENTS

| | | | |
|---|---|---|---|
| 3,402,298 | 9/1968 | Janeway | 358/107 X |
| 3,678,192 | 7/1972 | Akuta et al. | 358/107 |
| 4,258,388 | 3/1981 | Weisman et al. | 358/100 |
| 4,549,207 | 10/1985 | Boshier | 358/100 X |
| 4,980,763 | 12/1990 | Lia | 358/107 X |

Primary Examiner—Victor R. Kostak
Attorney, Agent, or Firm—Wall and Roehrig

[57] ABSTRACT

An elastomeric distance gage is formed of a ring of elastomeric film to which is joined a vee-shaped ear of elastomeric film. The ring of this gage fits removably onto a video head or other imager at the distal tip of a borescope. The legs of the nose portion converge to a distal tip which is within the viewing field of the borescope imager. To determine the size of an object, the gage is brought into contact with the object. The gage nose will deflect and this is visible in the viewing screen of the borescope. The object can be measured by comparison to a known width of the flat apex of the gage. Also, at this contact point, the object is a predetermined known distance from the borescope tip, and the size of the object can be determined by counting the number of pixels in the displayed image from one edge of the object to an opposite edge.

14 Claims, 2 Drawing Sheets

ELASTOMERIC GAGE FOR BORESCOPE

BACKGROUND OF THE INVENTION

This invention relates to improvements in borescopes or similar elongated probes. The invention is more particularly concerned with a technique which facilitates measurement of a target object in a concealed area which is in the viewing field of the borescope or similar probe.

A borescope is generally characterized as an elongated flexible insertion tube with a viewing head at its distal or forward tip and a control section at its proximal end for controlling the bending at the distal end. There are also hard or rigid probes which have a rigid insertion tube and do not flex at the distal tip. A viewing device, such as a video monitor can be employed to process picture information received from the viewing head and produce a visible image of a target object within the viewing field of the viewing head.

Generally, there are two classes of probes, based on the viewing system. A fiber probe has an optical imager and carries the image on a fiber optic bundle to the viewing device. A video probe has a miniature television camera contained in the probe distal tip and a video signal is carried on a conduit to a video monitor to display the image of the target object. This invention is applicable to either class of probe, and of either rigid or flexible design.

A borescope is generally intended for visual inspection of an intricate mechanical assembly, such as a jet engine, a turbine, or a heat exchanger tube, where it would be difficult or impossible otherwise to view the internal parts of the assembly. The borescope of the flexible type needs to be insertable into narrow, tortuous passageways and must observe very delicate steering considerations. Thus, any appendage on the tip of the borescope should have flexible characteristics so that it will not degrade the ability of the borescope to pass through these difficult passageways.

At the present time, feeler wires can be inserted through an instrument channel of a probe to contact a target area. This technique is applicable only to the probes that have an instrument channel, and such probes are typically of a greater diameter than optimal for inspection of many types of equipment. Also, the feeler wire technique does not lend itself to quick, reliable, and automated measurement of objects.

Another approach to distance and size measurement is described in copending U.S. patent application Ser. No. 364,883, filed June 12, 1989, having a common assignee herewith. This technique involves projecting a shadow onto the target object, and then determining the distance to the target based on the position of the shadow.

The borescope has an illumination source that is off the axis of the video imager, and projects a shadow or other auxiliary image onto the object that is illuminated for viewing. The position of the shadow gives distance information, which in turn yields magnification of the image on the screen of the video display. A pre-calibrated object magnification and distance scale can be established for the geometry of the borescope optics and for the distance determined by shadow position. The scale can be placed on the video display for measuring the dimensions of objects in the field of view. Size information can be gleaned automatically, based on the number of pixels from a predetermined screen position to the shadow position, and on the number of pixels, horizontally and vertically, across the target object.

In the case of a turbine or jet engine, the target object can be a small crack or fracture on a stator vane or rotor blade. This measurement technique is useful for an assessment of whether the crack is greater than some critical limit at which replacement would be necessary. This technique can also be employed to follow dimensional changes in critical parts as the system ages.

OBJECTS AND SUMMARY OF THE INVENTION

It is an object of this invention to provide a simple distance gage which facilitates measurement of objects in the field of view of a borescope or similar probe.

It is another object of this invention to provide a distance gage for very small diameter borescopes (i.e., 6 mm or smaller) which can be employed to measure the size of defects in jet engines.

It is a further object to provide a gage which does not interfere with insertion of the probe into a cavity, and which will not impair withdrawal of the probe from the cavity.

It is a more specific object of the invention to provide a gage in which a distal tip of the gage is brought into the field of view of the probe for scaling object size.

It is another object to provide a gage that does not add appreciably to the effective diameter of the probe head or to its effective length, and does not adversely affect operations of the probe.

In accordance with an aspect of this invention, a distance gage is fitted onto the distal tip of a borescope for measuring the size and distance of a target object in the field of view of the borescope. The gage comprises a ring portion that fits removably onto a generally tubular distal tip of the borescope, and a resilient flexible ear that projects axially from the ring portion a predetermined distance distally, i.e., in advance of the borescope viewing head. Preferably, the ring member and ear are unitarily formed of an elastomeric material. The ear can be generally triangular with an open window cut through. The ear can be in the form of a vee, whose legs converge to an apex distal of the ring portion. The apex can have a transverse edge of a predetermined width for gaging directly the size of objects.

The gage will deflect and bend to permit the borescope to pass through narrow passageways, and then will spring back to its normal position when the obstruction is passed.

When the probe is moved towards the object, the gage will deflect noticeably when the tip of the gage contacts the object. At that time, the object is at a distance from the probe tip that equals the length of the ear of the gage. For a given borescope system, the magnification is known for each given distance, and the dimensions of the object can be measured on the screen directly, by applying an appropriate scaling factor.

The size of the object can also be measured electronically. The probe is first adjusted to be positioned where the distal end of the gage just contacts the target object, while the operator is monitoring the image in the display device. This position will be evident in that there is a clearly visible deflection of the ear of the gage when the gage ear touches the object. Then, the operator actuates the monitor device to capture the video image electronically. The operator can move a cursor to end points of the image of the target object, i.e., edges of a crack or pit. Then, the number of picture elements (pixels) is counted, both horizontally and vertically, between the cursor positions. The scaling factor is known for this probe-to-object distance, and the number of pixels can be converted to a distance.

The size of the object also can be measured directly by comparing with the width of a flat, transverse edge at the distal end of the gage ear.

The above and many other objects, features, and advantages of this invention will be more fully appreciated from the ensuing description of a preferred embodiment, to be read in connection with the accompanying Drawing.

DETAILED DESCRIPTION OF THE PREFERRED EMBODIMENT

Figure 1:
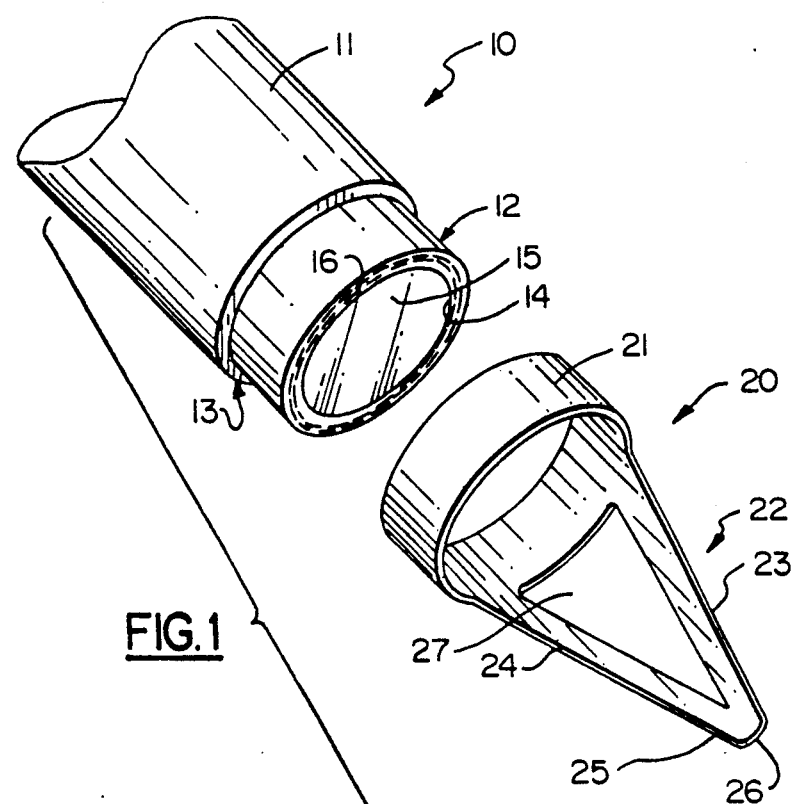
FIG. 1 is a schematic perspective view of a borescope probe and a gage thereof.
Figure 2:
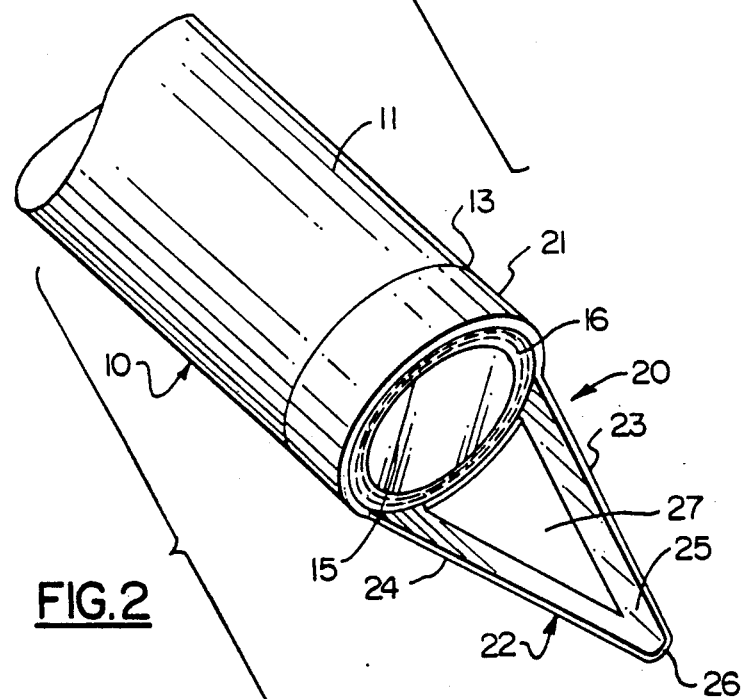
FIG. 2 is a similar view showing the gage attached to the borescope.

With reference to the Drawing, and initially to FIG. 1, an operative portion of a borescope 10 is shown, comprising an insertion tube 11 at a distal tip of which is mounted a viewing head 12 of the video type. The head 12 is generally cylindrical, with a shoulder or step 13 therein located a predetermined length proximally of the distal edge. At the distal edge of the head 12 there is a front or face plate 14 behind which is located a video imager 15, which is a miniature television camera with self contained optics, and a fiber optic bundle 16, which is connected to a light source (not shown) in a video processor unit. Terminal ends of the fibers of this bundle 16 are arranged in a circle around the periphery of the imager 15. The bundle 16 provides illumination to a remote target which is in the field of view of the imager 15.

A distance gage 20 for this borescope 10 is in the form of a cap formed of an elastomeric film. The gage 20 has a ring or band 21 that fits securely but removably over the viewing head 12 and against the shoulder 13 for accurately locating or positioning the gage 20. A generally triangular ear 22 projects distally from the ring 21 so that it is in the viewing field of the video imager 15. Here, the ear 22 is in the form of a vee with a pair of legs 23 and 24 that converge to an apex 25 located distally from the ring 21. The apex 25 has a flat transverse distal edge 26 of a predetermined width. As this distal edge 26 is visible to the operator viewing the image provided by the imager 15, this edge 26 can be used for direct measurement of objects that it is placed against. The transverse edge can have a width, e.g., of 0.125".

The two legs 23 and 24 also define a triangular window 27 which permits viewing of a portion of the field of view that is below the apex 25.

In this embodiment, the legs 23 and 24 have their open end connected to the ring 21 circumferentially part way up the side from the bottom. This ensures that the normal position of the ear 22 is not flat, nor are the legs 23 and 24 in parallel planes. The ear 22 is curled somewhat around the longitudinal axis, with a stiffening component of support. However, the ear 22 will flex to permit it to bend when obstacles are encountered in the passage to the target area. This arrangement provides good lateral or side-to-side support, good radial support, and good longitudinal support. An included angle between the legs of approximately 90 degrees has been found to be satisfactory.

Figures 3, 4:
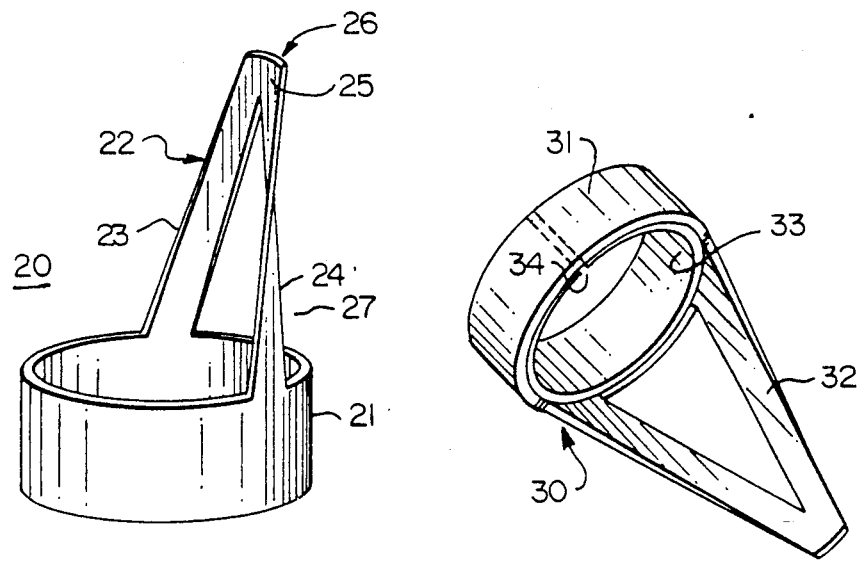
FIG. 3 is a perspective view of an elastomeric gage according to one embodiment of this invention.
FIG. 4 is a perspective view of a gage according to an alternative embodiment.

As shown in FIG. 4, an alternative gage 30 has an outer ring 31 formed of an elastomeric film and a vee-shaped ear, similar to the previous embodiment. In this case, an aluminum inner ring 33 is provided to fit onto the viewing head 12. The elastomeric ring 31 is secured by an adhesive to the aluminum ring 33. A longitudinal or axial slot 34 is cut into the ring on the side opposite the ear 32, and this slot can also pass, if desired, through the elastomeric ring 31 as well.

With either of the embodiments of FIG. 3 or FIG. 4, the gage 20 or 30 will release from the borescope 10 if caught or snagged within a passageway. Because the gage is formed entirely of a soft, combustible elastomeric material or elastomeric material and soft aluminium, the gage can be left inside a turbine or jet engine and will be completely consumed in operation of the turbine or jet engine, without causing damage.

Figure 5:
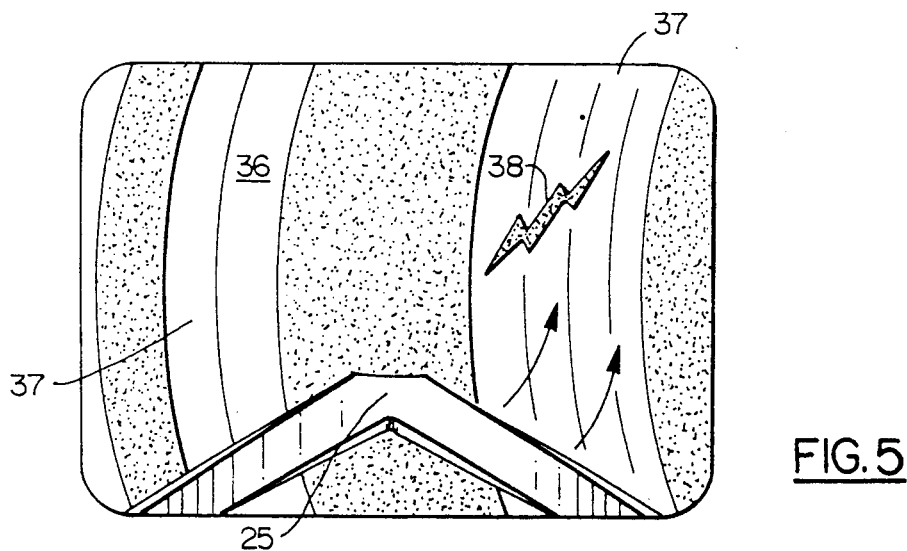
FIGS. 5 and 6 show a screen display of a video monitor associated with a borescope on which the gage of this invention is employed.

With the gage 20 properly located and positioned on its tip, the borescope 10 can be inserted through the passageway into the target area. The ear 22 will flex and bend to permit the borescope 10 to be pushed past any obstacles. When the borescope tip is within the target area, the borescope will produce a video image on a video screen 36, as generally shown in FIG. 5. In this case, the ear 22 of the gage is clearly visible at the bottom of the screen 36, as the borescope 10 approaches a target object 37. In this example, the target object can be a stator vane of a jet engine or turbine, and can have a mark, such as a crack or scar 38 on the surface of the vane 37.

Figure 6:
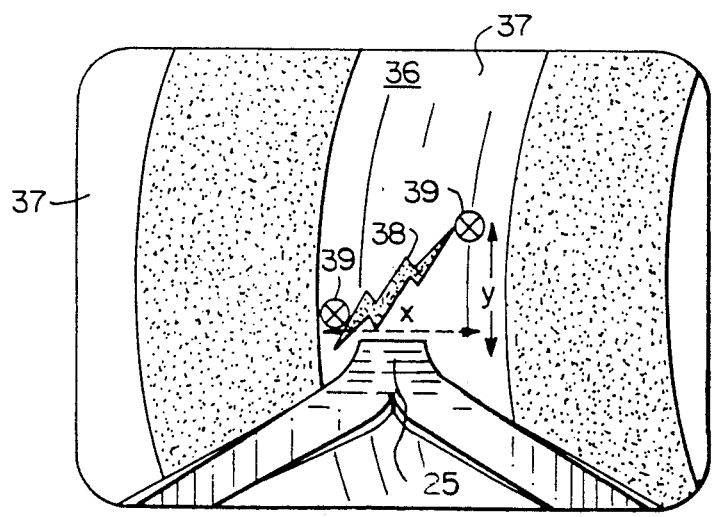

As shown in FIG. 6, when the apex or tip 25 of the gage ear 22 contacts against the target object, the apex 25 and ear 22 will deflect, and this event is clearly visible on the video screen. At this point, the target object 37 is at a predetermined distance from the borescope imager 15, which corresponds to the length of the gage ear 22. For a given optics package in the imager 15, and for a given target distance, there will be a known magnification, i.e., ratio of the screen image to the size of the target object. At the time of the deflection of the gage tip or apex 25, the operator can actuate a freeze switch and electronically capture this image on the screen 36.

After this, the operator can place electronic cursors at the ends of the crack 38, or at other positions across which a dimension of interest is desired. These two cursors 39 are separated by a given number of picture elements or pixels in the left-to-right direction, and are also separated by a given number of video lines in the vertical direction. By counting the number of pixels and the number of lines, a horizontal or x distance and a vertical or y distance can be determined. The total length between the cursors 39 is simply the square root of the sum of the squares of the x distance and y distance. This is true so long as the plane of the target 37 is nearly perpendicular to the optical axis of the borescope imager 15.

While this invention has been described in detail to a selective preferred embodiment, it should be understood that the invention is not limited to that precise embodiment. Rather, many modifications and variations would present themselves to those of skill in the art without departing from the scope and spirit of this invention, as defined in the appended claims.

What is claimed is:

1. Gage for measuring size and distance of a target object viewed in a borescope probe which has a viewing head at a distal tip of a tubular probe member, the gage comprising a ring fitting removably over said distal tip and a resiliently flexible ear projecting axially from said ring a predetermined distance distal of said viewing head.

2. Gage according to claim 1 wherein said ring and said ear are unitarily formed of an elastomeric material.

3. Gage according to claim 1 wherein said ear is generally triangular with an open window cut therethrough.

4. Gage according to claim 1 wherein said ear is in the form of a vee having a pair of legs that converge to an apex distal of the ring.

5. Gage according to claim 4 wherein said legs join said ring at a circumferential included angle of about 90 degrees.

6. Gage according to claim 1 wherein said apex has a flat transverse edge of a predetermined width.

7. Gage according to claim 2 wherein an inner non-elastomeric ring is contained within said elastomeric ring.

8. Gage according to claim 7 wherein said inner non-elastomeric ring is slit generally axially.

9. Gage according to claim 7 wherein both said elastomeric ring and said non-elastomeric ring are slit generally axially.

10. In combination, a borescope of the type which has an elongated insertion tube, and a viewing head at a distal tip of said insertion tube which obtains an image of an object in a viewing field distally of said tip and transmits same to a viewing device; and a gage for measuring size and distance of said object; said gage including a ring fitting removably over said distal tip and a flexible resilient ear projecting axially from said ring a predetermined distance distal of said viewing head.

11. The combination of claim 10 wherein said ring and said ear are unitarily formed of an elastomeric material.

12. The combination of claim 10 wherein said ear is in the form of a vee having a pair of legs that converge to an apex a predetermined distance distal of said viewing head.

13. The combination of claim 12 wherein said apex has a flat transverse edge of a predetermined width.

14. Method of measuring the size of an object that is within the viewing area of a video borescope of the type in which a viewing head is positioned at the distal tip of a probe insertion tube, the viewing head producing an image that is transmitted to a viewing device and presented as an array of picture elements and wherein a gage is removably fitted onto said distal tip, said gage including a ring fitting removably over said distal tip and a flexible resilient ear that extends distally to a distal edge a predetermined distance distal of said viewing head such that said ear appears in the image in the viewing device; the method comprising:

a. positioning said insertion tube distal tip so that the distal edge of the ear contacts said object, while monitoring the image in said viewing device;

b. electronically capturing the image of said object in said viewing device when said ear is in contact with said object, so that said object is at substantially said predetermined distance from said viewing head;

c. electronically counting the picture elements from one edge of said object to an opposite edge in at least one direction; and d. computing the size of said object based on the number of picture elements and the length of said predetermine distance.

* * * * *